United States Patent
Simonnet et al.

(10) Patent No.: US 6,565,886 B1
(45) Date of Patent: May 20, 2003

(54) NANOCAPSULES BASED ON POLY (ALKYLENE ADIPATE), PROCESS FOR THEIR PREPARATION AND COSMETIC OR DERMATOLOGICAL COMPOSITIONS CONTAINING THEM

(75) Inventors: Jean-Thierry Simonnet, Paris (FR); Pascal Richart, Paris (FR); Bruno Biatry, Vincennes (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/467,897

(22) Filed: Dec. 21, 1999

(30) Foreign Application Priority Data

Dec. 29, 1998 (FR) .............................................. 98 16554

(51) Int. Cl.⁷ ................................................. A61K 9/14
(52) U.S. Cl. ........................ 424/489; 424/401; 424/490
(58) Field of Search ................................ 424/401, 489, 424/490

(56) References Cited

U.S. PATENT DOCUMENTS 5,766,637 A * 6/1998 Shine et al. ................. 424/497
5,919,487 A * 7/1999 Simonnet et al. ........... 424/490

FOREIGN PATENT DOCUMENTS

| EP | 0 254 447 A | 1/1988 |
| EP | 0 274 961 A | 7/1988 |
| EP | A-378936 | 12/1989 |
| EP | 0 447 318 A | 9/1991 |
| EP | A-570-230 | 5/1993 |
| FR | A-2581542 | 5/1985 |
| FR | 2 681 248 | 3/1993 |
| FR | 2 742 677 A1 * | 12/1995 |
| JP | 0 1071823 | 3/1989 |
| WO | WO 96/31194 | 10/1996 |

OTHER PUBLICATIONS

DATABASE WPI, Section Ch, Week 8917, Derwent Publications Ltd., London, GB, AN 89–126027 (English abstract of JP 01071823).

* cited by examiner

Primary Examiner—Jose' G. Dees
Assistant Examiner—Konata M George
(74) Attorney, Agent, or Firm—Nixon & Vanderhye P.C.

(57) ABSTRACT

The present invention relates to nanocapsules consisting
  of a lipid centre forming or containing a lipophilic active principle, and
  of a water-insoluble continuous envelope comprising at least one polyester of poly(alkylene adipate) type
as well as to cosmetic and/or dermatological compositions containing the said nanocapsules based on poly(alkylene adipate).

33 Claims, No Drawings

NANOCAPSULES BASED ON POLY (ALKYLENE ADIPATE), PROCESS FOR THEIR PREPARATION AND COSMETIC OR DERMATOLOGICAL COMPOSITIONS CONTAINING THEM

The present invention relates to nanocapsules based on polyesters of poly(alkylene adipate) type, to a process for their preparation and to cosmetic or dermatological compositions containing them.

The encapsulation or absorption of lipophilic active principles in particles of submicron dimensions has been known for several years and is widely used in particular in the fields of cosmetology and dermatology. Specifically, these particles, known as nano-particles, are capable of crossing the superficial layers of the stratum corneum and of penetrating into the upper layers of the living epidermis to release the active principle therein. This penetration into deeper layers broadens the space of action of the active principles and shelters them from rapid elimination by simple rubbing.

The term "nanoparticles" mainly encompasses two different systems: "nanospheres" consisting of a porous polymer matrix in which the active principle is absorbed and/or adsorbed, and "nanocapsules" with a structure of core-envelope type, i.e. a structure consisting of a lipid centre forming or containing the active principle, this centre being encapsulated in a water-insoluble continuous protective envelope. The present invention relates exclusively to this second vesicular type of nanoparticles, i.e. nanocapsules with a lipid core surrounded by a polymer membrane.

The encapsulation of active principles in capsules of submicron size makes it possible, admittedly, to transport the active molecules more deeply into the skin, but—contrary to what this "protective" structure might lead one to think—it does not always provide the active principle with sufficient stability with respect to the surrounding physico-chemical conditions.

The problem of the instability of the active principle arises in particular for substances which are sensitive to oxidation, light, high temperatures and/or acidic or basic pHs. Such a substance, which is very commonly used in cosmetics, is, for example, retinol (vitamin A) which is sensitive to oxidation in particular at acidic pH.

One approach for stabilizing retinol consists in adding lipophilic antioxidants and chelating agents to the compositions containing it and in adjusting the pH of these compositions to a value of between 5 and 10 (WO 96/31194).

The Applicant has discovered that encapsulation in nanocapsules based on a specific type of polymer makes it possible to improve the stability of retinol spectacularly, in particular in the absence of antioxidants.

The polymers which make it possible to obtain such a favourable effect are polyesters of poly(alkylene adipate) type described in greater detail below.

Thus, the encapsulation of retinol in nanocapsules with an envelope formed from polyesters of poly(alkylene adipate) type gives this active molecule satisfactory stability, i.e. a loss of activity of only 5 to 10% after storage for 2 months at 45° C., whereas, under equivalent conditions, this same molecule encapsulated in other polymers commonly used for nanoencapsulation (for example polycaprolactone or cellulose derivatives) has a loss of activity of greater than 20%.

One subject of the invention is thus nanocapsules consisting
of a lipid centre forming or containing a lipophilic active principle, and
of a water-insoluble continuous polymeric envelope comprising at least one polyester of poly(alkylene adipate) type.

Another subject of the invention is cosmetic and/or dermatological compositions containing the said nanocapsules based on poly(alkylene adipate).

Another subject of the invention is a process for preparing the above nanocapsules based on poly(alkylene adipate).

Other subjects will become apparent on reading the description and the examples which follow.

The polyesters which can be used to form the envelope for the nanocapsules are polymers obtained by polycondensation of an aliphatic dicarboxylic acid, namely adipic acid (hexane-1,6-dioic acid), and of one or more diols and, optionally, of a small proportion of triols.

The term poly(alkylene adipate) used in the present patent application to denote the polyesters forming the envelope of the nanocapsules encompasses both homopolymers of adipic acid and of an alkanediol and copolymers of linear or branched poly(ester ether) type, obtained from adipic acid and from one or more alkanediols and/or ether-diols and/or triols.

The alkanediols used for the preparation of the said poly(alkylene adipates) are $C_2$–$C_6$ alkanediols with a linear or branched chain, chosen from ethylene glycol, propylene glycol, 1,3-propanediol, 1,4-butanediol, 1,5-pentanediol, 1,6-hexanediol and neopentyl glycol.

The ether-diols are di, tri- or tetra($C_2$–$C_4$ alkylene) glycols, such as diethylene glycol, triethylene glycol, tetraethylene glycol, dipropylene glycol, tripropylene glycol, tetrapropylene glycol or dibutylene glycol, tributylene glycol or tetrabutylene glycol.

As indicated above, the polyesters of poly(alkylene adipate) type used for the preparation of the nanocapsules of the invention can also contain a limited number of branching units derived from triols.

The triols used are generally chosen from glycerol, trimethylolethane, and trimethylolpropane.

The fraction of the branching units derived from the above triols generally does not exceed 5 mol % relative to the total number of units derived from diols and triols.

According to one preferred embodiment of the present invention, the envelope for the nanocapsules is formed from a poly(ethylene adipate) or from a poly(butylene adipate).

The poly(alkylene adipates) used in the present invention have a weight-average molar mass (measured by gel permeation chromatography) of between 2000 and 50,000, preferably between 5000 and 15,000.

This molar mass range is limited on the one hand, for low masses, by an excessive content of residual oligomers and monomers, and, for high masses, by an unacceptable production cost.

The poly(alkylene adipates) used in the present invention are known and can be prepared according to known processes.

A whole range of products of different chemical composition and of different mass is sold under the name Fomrez® by the company Witco. The company Scientific Polymer Products sells, under the name Poly(ethylene)adipat®, a poly(ethylene adipate) with a weight-average molar mass (determined by GPC) of about 10,000.

The polyesters of poly(alkylene adipate) type as described above are used to prepare nanocapsules consisting of a lipid centre forming or containing a lipophilic active principle surrounded by an envelope formed from these polymers.

The process for preparing nanocapsules which is preferably used by the Applicant is the one described in EP-A-0, 274,961 and comprises the steps consisting in dissolving the polymer, the lipid phase forming or containing the active principle, and optionally a surfactant which acts as coating agent, in a suitable organic solvent, i.e. a solvent which is miscible with water, non-toxic and more volatile than water (generally acetone and/or a lower alcohol), in preparing a solution of a suitable surfactant in water (which is a non-solvent for the polymer and the lipid phase), in adding the organic phase to the aqueous phase with moderate stirring thereof, which results in the spontaneous formation of a nanocapsule emulsion, and then in evaporating the organic phase and, possibly, some of the aqueous phase, in order to obtain a concentrated suspension of nanocapsules in an aqueous phase.

This preparation process generally involves heating the organic phase and/or the aqueous phase to temperatures of between 35 and 70° C. The poly(alkylene adipates) used in the present invention make it possible to carry out this process at room temperature, which constitutes an important advantage in particular for heat-sensitive active substances such as retinol.

The surfactant dissolved in the aqueous phase serves mainly to control the size of the nanocapsules. The reason for this is that it ensures the stability of the nanocapsules in the emulsion resulting from the addition of the acetone phase to the aqueous phase, and prevents them from coalescing.

Any surfactant of hydrophilic nature, whether nonionic, anionic or cationic, can be used. Mention may be made, for example, of sodium lauryl sulphate, quaternary ammonium compounds, polyoxyethylenated or non-polyoxyethylenated sorbitan monoesters, fatty alkyl ethers of a polyoxyethylene glycol, the condensates of ethylene oxide and of propylene oxide, such as the product Pluronic® F-68 sold by the company BASF, or phospholipids such as lecithin.

The weight ratio of the surfactant to the materials constituting the nanocapsules is advantageously between 0.01 and 0.5 and preferably in the region of 0.2.

It is often desirable or necessary to provide the nanocapsules with a so-called "lamellar" coating. This is a structure organized as one or more lipid lamella(e) each consisting of a bilayer of amphiphilic molecules which is similar to that of biological membranes.

Besides its function of adjusting the size of the nanocapsules, this coating improves the leaktightness of the nanocapsules with respect to a leakage of the active principle into another lipid phase of the composition.

The coating agents are surfactants of hydrophobic nature, which are soluble in the organic phase and which are capable, in the presence of water, of forming the lipid double-layers described above. In the process for encapsulating active principles, used by the Applicant, this coating agent is dissolved in the organic (acetonic/alcoholic) phase containing the polymer and the lipid phase.

Examples of such coating agents which may be mentioned are phospholipids such as lecithin according to patent application EP-A-447,318, certain polycondensates of ethylene oxide and of propylene oxide, such as the products sold under the name Pluronic® by the company BASF, such as Pluronic® L121 or under the name Synperonic® by the company ICI, or certain silicone surfactants, such as those described in documents U.S. Pat. No. 5,364,633 and U.S. Pat. No. 5,411,744 and used in patent application FR-A-2,742,677, for example those sold by the company Dow Corning under the names DC 5329, DE 7439-146, DC 2-5695 and Q4-3667.

The average size of the nanocapsules based on poly (alkylene adipate) thus obtained is advantageously between 50 and 800 nm, preferably between 100 and 300 nm. This size is determined, for example, using a laser granulometer (Amtech BI90 model from the company Brookhaven Instrument).

The nanocapsules of the present invention can contain lipophilic cosmetic or dermatological active principles of any kind.

Examples which may be mentioned are emollients, anti-inflammatory agents, antibacterial agents, antifungal agents, antiviral agents, anti-seborrhoeic agents, anti-acne agents, keratolytic agents, antihistaminic agents, anaesthetics, cicatrizing agents, pigmentation modifiers, sunscreens, free-radical scavengers, moisturizers, vitamins and other similar lipophilic compounds.

According to the present invention, the encapsulated active principle is preferably a lipophilic active principle which is sensitive to the surrounding physicochemical conditions such as the temperature, pH, light or the presence of oxidizing agents.

Examples of preferred lipophilic active principles which may be mentioned are vitamins such as vitamin A (retinol) or esters thereof, vitamin E or esters thereof, such as tocopheryl acetate, vitamin D or derivatives thereof and vitamin F or derivatives thereof, carotenes such as β-carotene or derivatives thereof, for instance lycopene, and salicylic acid or derivatives thereof, in particular those described in documents FR-A-2,581,542, EP-A-378,936 and EP-A-570,230, in particular 5-n-octanoylsalicylic acid, 5-n-decanoylsalicylic acid, 5-n-dodecanoylsalicylic acid, 5-n-octylsalicylic acid, 5-n-heptyloxysalicylic acid and 4-n-heptyloxysalicylic acid.

Excellent results have been obtained in particular for encapsulating retinol (vitamin A), a molecule which is very sensitive to oxidation at acidic pH, as well for the $C_1$–$C_{30}$, more particularly $C_1$–$C_6$ as esters thereof, such as retinyl acetate and retinyl propionate.

Another subject of the present invention is cosmetic or dermatological compositions containing, in a physiologically acceptable support, the nanocapsules based on poly (alkylene adipate) described above.

The fraction represented by the nanocapsules in the cosmetic and/or dermatological compositions of the present invention is generally between 0.1 and 30% by weight and preferably between 0.5 and 15% by weight, relative to the total weight of the composition.

In addition to the nanocapsules and the aqueous phase, the compositions can contain known cosmetic and/or pharmaceutical adjuvants, such as fatty substances, petroleum jelly, pH regulators, preserving agents, thickeners, dyes or fragrances.

Needless to say, a person skilled in the art will take care to select this or these optional additional compound(s) and the amount thereof such that the advantageous properties intrinsically associated with the cosmetic or dermatological composition in accordance with the invention are not, or are not substantially, adversely affected by the addition(s) envisaged.

The compositions according to the invention can, for example, be in the form of an aqueous, aqueous-alcoholic or oily serum, lotion or gel, a water-in-oil or oil-in-water emulsion or alternatively in the form of aqueous dispersions of lipid vesicles consisting of ionic or nonionic lipids or of a mixture thereof, these vesicles containing or not containing an oily phase.

The examples given below, purely for the purposes of illustration and without any implied limitation, will allow the invention to be understood more clearly.

EXAMPLE 1

Preparation of Nanocapsules Based on Poly (Ethylene Adipate)

The following products:

1 g of poly(ethylene adipate) from the company Scientific Polymer Products, and 1 g of Pluronic® L121 sold by the company BASF are dissolved in 150 ml of acetone in a 500 ml amber-glass round-bottomed flask under inert atmosphere, at room temperature and with stirring.

Separately, 5 g of capric acid and caprylic acid triglycerides (lipid phase) containing 10% retinol are dissolved in 50 ml of acetone in a 250 ml amber-glass round-bottomed flask under inert atmosphere and in actinic light, at room temperature and with stirring.

This second solution is added to the contents of the 500 ml flask.

0.5 g of a nonionic surfactant (triblock polycondensate of ethylene oxide and propylene oxide, sold under the name Pluronic® F68 by the company BASF) is dissolved in 300 g of distilled water in a 1 amber-glass round-bottomed flask under inert atmosphere and at room temperature.

The acetone phase is added to the aqueous phase with continued stirring.

The acetone and some of the water are then evaporated off in a rotary evaporator, down to a final volume of 100 ml.

This aqueous suspension contains nanocapsules with an average diameter of 250 nm.

EXAMPLE 2

Preparation of Nanocapsules Based on Poly (Butylene Adipate)

The process is performed as described in Example 1, but replacing the poly(ethylene adipate) with an identical amount by weight of poly(butylene adipate) sold by the company Aldrich.

An aqueous suspension of nanocapsules based on poly (butylene adipate) with an average diameter of 270 nm is obtained.

EXAMPLE 3

Tests of Stability of Retinol Encapsulated in Various Polymers

The stability of the retinol enclosed in the nanocapsules based on poly(ethylene adipate) (obtained in Example 1) is compared with the stability of this active principle in nanocapsules based on known polymers, namely polycaprolactone and cellulose acetobutyrate, which are coated with a nonionic surfactant.

The nanocapsules containing retinol are stored in the form of an aqueous suspension for two months at 45° C. in closed packagings which are leaktight with respect to light and gases. After this storage period, the loss of active principle (retinol) is evaluated by HPLC after detection at 325 nm.

The results obtained are collated in the following table.

| Polymer | Poly(ethylene adipate) | Poly(capro-lactone) | Cellulose acetobutyrate |
|---|---|---|---|
| Molar mass of the polymer | 10,000 | 50,000 | 30,000 |
| m.p. of the polymer (in ° C.) | 55 | 58–60 | 155–165 |
| Coating agent | nonionic surfactant* | nonionic surfactant* | nonionic surfactant* |
| Average diameter of the nanocapsules | 243 nm | 266 nm | 213 nm |
| pH of the composition | 8.7 | 6.4 | 6.1 |
| Loss of active principle after two months at 45° C. | 6% | 28% | 21% |

*Pluronic ® L121 sold by the company BASF.

These results show that the use of poly(ethylene adipate) for the preparation of nanocapsules significantly improves the stability to oxidation of the encapsulated retinol.

What is claimed is:

1. Nanocapsules comprising
a lipid center forming or containing a lipophilic active principle, and
a water-insoluble continuous polymeric envelope,
wherein said polymeric envelope comprises at least one linear or branched poly(alkylene adipate) polyester comprising units derived from adipic acid and units derived from at least one compound selected from the group consisting of alkanediols, ether-diols and triols.

2. Nanocapsules according to claim 1, wherein the alkanediol is a $C_2$–$C_6$ alkanediol with a linear or branched chain, selected from the group consisting of ethylene glycol, propylene glycol, 1,3-propanediol, 1,4-butanediol, 1,5-pentanediol, 1,6-hexanediol and neopentyl glycol.

3. Nanocapsules according to claim 1 wherein the ether-diol is a di-, tri- or tetra($C_2$–$C_4$ alkylene) glycol selected from the group consisting of di-, tri- or tetraethylene glycol, di.-, tri- or tetrapropylene glycol and di-, tri- or tetrabutylene glycol.

4. Nanocapsules according to claim 1 wherein the triol is glycerol, trimethylolethane or trimethylolpropane.

5. Nanocapsules according to claim 1 wherein the units derived from at least one triol represents not more than 5 mol % of the total amount of units derived from diols and triols.

6. Nanocapsules according to claim 1 wherein the polyesters forming the envelope are linear poly(butylene adipates) or poly(ethylene adipates).

7. Nanocapsules according to claim 1 wherein the polyesters forming the envelope have a weight-average molar mass, measured by gel permeation chromatography, of between 2000 and 50,000.

8. Nanocapsules according to claim 1 wherein the polymeric envelope is surrounded by a lamellar coating which has a structure organized as one or more lamella(e) each consisting of a double-layer of amphiphilic molecules said lamellar coating being a coating agent.

9. Nanocapsules according to claim wherein 8, wherein said coating agent is selected from the group consisting of phospholipids, polycondensates of propylene oxide and of ethylene oxide, and silicone surfactants, which are capable of forming lamellar structures.

10. Nanocapsules according to claim 1, wherein said nanocapsules have an average size of between 50 nm and 800 nm.

11. Nanocapsules according to claim 1 wherein the encapsulated lipophilic active principle is selected from the group consisting of emollients, anti-inflammatory agents, antibacterial agents, antifungal agents, antiviral agents, anti-seborrhoeic agents, anti-acne agents, keratolytic agents, anti-histaminic agents, anaesthetics, cicatrizing agents, pigmentation modifiers, sunscreens, free-radical scavengers, moisturizers and vitamins.

12. Nanocapsules according to claim 11, wherein the encapsulated lipophilic active principle is selected from the group consisting of lipophilic active principles which are sensitive to the surrounding physicochemical conditions.

13. Nanocapsules according to claim 12, wherein the lipophilic active principle is selected from the group consisting of vitamins or esters or derivatives thereof, carotenes or derivatives thereof, and salicylic acid or derivatives thereof.

14. Nanocapsules according to claim 13, wherein the lipophilic active principle is retinol or a $C_1$–$C_{30}$ ester thereof.

15. Cosmetic or dermatological composition comprising, in a physiologically acceptable support, the nanocapsules according to claim 1.

16. Cosmetic or dermatological composition according to claim 15, wherein the fraction of nanocapsules is between 0.1 and 30% by weight relative to the total weight of the composition.

17. Cosmetic or dermatological composition according to claim 15 further comprising at least one cosmetic or pharmaceutical adjuvant.

18. Cosmetic or dermatological composition according claim 15, in the form of an aqueous, aqueous-alcoholic or oily serum, lotion or gel, a water-in-oil or oil-in-water emulsion, or an aqueous dispersion of lipid vesicles consisting of ionic or nonionic lipids or of a mixture thereof, said lipid vesicles optionally containing an oily phase.

19. Process for preparing the nanocapsules according to claim 1 comprising dissolving a polymer, a lipid phase forming or containing an active principle, and optionally a coating agent, in a water-miscible organic solvent, preparing an aqueous solution of a surfactant, adding the organic phase to the aqueous phase with moderate stirring, and then evaporating the organic phase and, optionally, a portion of the aqueous phase, said polymer being at least one linear or branched poly(alkylene adipate) polyester comprising units derived from adipic acid and units derived from at least one compound selected from the group consisting of alkanediols, ether-diols and triols.

20. Nanocapsules according to claim 7 wherein weight-average molar mass is between 5000 and 15,000.

21. Nanocapsules according to claim 9, wherein said phospholipids is lecithin.

22. Nanocapsules according to claim 10, wherein said nanocapsules have an average size of between 100 nm and 300 nm.

23. Nanocapsules according to claim 12, wherein said physicochemical conditions are selected from the group consisting of temperature, pH, light and the presence of oxidizing agents.

24. Nanocapsules according to claim 13, wherein said lipophilic active principle is selected from the group consisting of vitamin A, vitamin E, vitamin D and vitamin F, or esters or derivatives of vitamins A, E, D and F, β-carotene, lycopene, 5-n-octanoylsalicylic acid, 5-n-decanoylsalicylic acid, 5-n-dodecanoylsalicylic acid, 5-n-octylsalicylic acid, 5-n-heptyloxysalicylic acid, 4-n-heptyloxysalicylic acid and derivatives of β-carotene, lycopene, 5-n-octanoylsalicylic acid, 5-n-decanoylsalicylic acid, 5-n-dodecanoylsalicylic acid, 5-n-octylsalicylic acid, 5-n-heptyloxysalicylic acid, and 4-n-heptyloxysalicylic acid.

25. Nanocapsules according to claim 14, wherein the lipophilic active principle is retinol or a $C_1$–$C_6$ ester thereof.

26. Nanocapsules according to claim 25 wherein the lipophilic active principle is retinyl acetate or retinyl propionate.

27. Cosmetic or dermatological composition according to claim 16, wherein the fraction of nanocapsules is between 0.5 and 15% by weight, relative to the total weight of the composition.

28. Cosmetic or dermatological composition according to claim 17 wherein the at least one cosmetic or pharmaceutical adjuvant is selected from the group consisting of fatty substances, petroleum jelly, pH regulators, preserving agents, thickeners, dyes and fragrances.

29. Nanocapsules comprising a lipid center forming or containing a lipophilic active principle which is sensitive to the surrounding physiochemical conditions, and a water-insoluble continuous polymeric envelope, wherein said polymeric envelope comprises at least one linear or branched poly(alkylene adipate) polyester comprising units derived from adipic acid and units derived from at least one compound selected from the group consisting of alkanediols, ether-diols and triols.

30. Nanocapsules comprising a lipid center forming or containing a lipophilic active principle, and a water-insoluble continuous polymeric envelope comprising at least one poly(ethylene adipate).

31. Nanocapsules of claim 29 wherein said poly(alkylene adipate) is a poly(ethylene adipate).

32. Nanocapsules of claim 29 wherein said lipophilic active principle is retinol.

33. Nanocapsules of claim 30 wherein said lipophilic active principle is retinol.

* * * * *